United States Patent
Bergner et al.

[11] Patent Number: 5,914,770
[45] Date of Patent: Jun. 22, 1999

[54] OPHTHALMOLOGICAL EXAMINATION INSTRUMENT AND METHOD FOR OPERATION THEREOF

[75] Inventors: Roland Bergner; Klaus-Ditmar Voigt; Frank Teige; Ingo Koschmieder, all of Jena, Germany

[73] Assignee: Carl Zeiss Jena GmbH, Jena, Germany

[21] Appl. No.: 08/880,078

[22] Filed: Jun. 20, 1997

[30] Foreign Application Priority Data

May 17, 1997 [DE] Germany .................... 197 20 851

[51] Int. Cl.⁶ ........................................... A61B 3/14
[52] U.S. Cl. ............................................. 351/206
[58] Field of Search .................... 351/205, 200, 351/206, 207, 210, 211, 216, 221, 246; 396/18

[56] References Cited

U.S. PATENT DOCUMENTS

| | | | |
|---|---|---|---|
| 5,140,352 | 8/1992 | Moore et al. | 351/206 |
| 5,225,859 | 7/1993 | Fleischman | 351/206 |
| 5,374,967 | 12/1994 | Hideshima et al. | 351/206 |
| 5,394,199 | 2/1995 | Flower | 351/206 |

*Primary Examiner*—George Manuel
*Attorney, Agent, or Firm*—McAulay Nissen Goldberg Kiel & Hand, LLP

[57] ABSTRACT

An ophthalmological examination device, especially a slit lamp or a fundus camera, for observing a patient's eye, with at least one image recording unit such as a video camera or a CCD-chip for recording at least a part of the image of the eye generated by the examination device, and with a device for transmitting the electric signals of the video camera or CCD-chip to an image generating unit connected with the head of the observer.

In an advantageous manner, it is possible to superimpose on a first image generated from the electric signals of an image recording unit additional information generated by a computer via the image generating unit, at least for one eye of the observer, and/or to display a second image to the observer, which second image is modified with respect to color, contrast or other image features, as an additional image superimposed on the other respective eye or on the first image for one or both eyes of the observer. The additional information comprises stored images and/or stored previous recordings and/or physiological data on the patient.

22 Claims, 7 Drawing Sheets

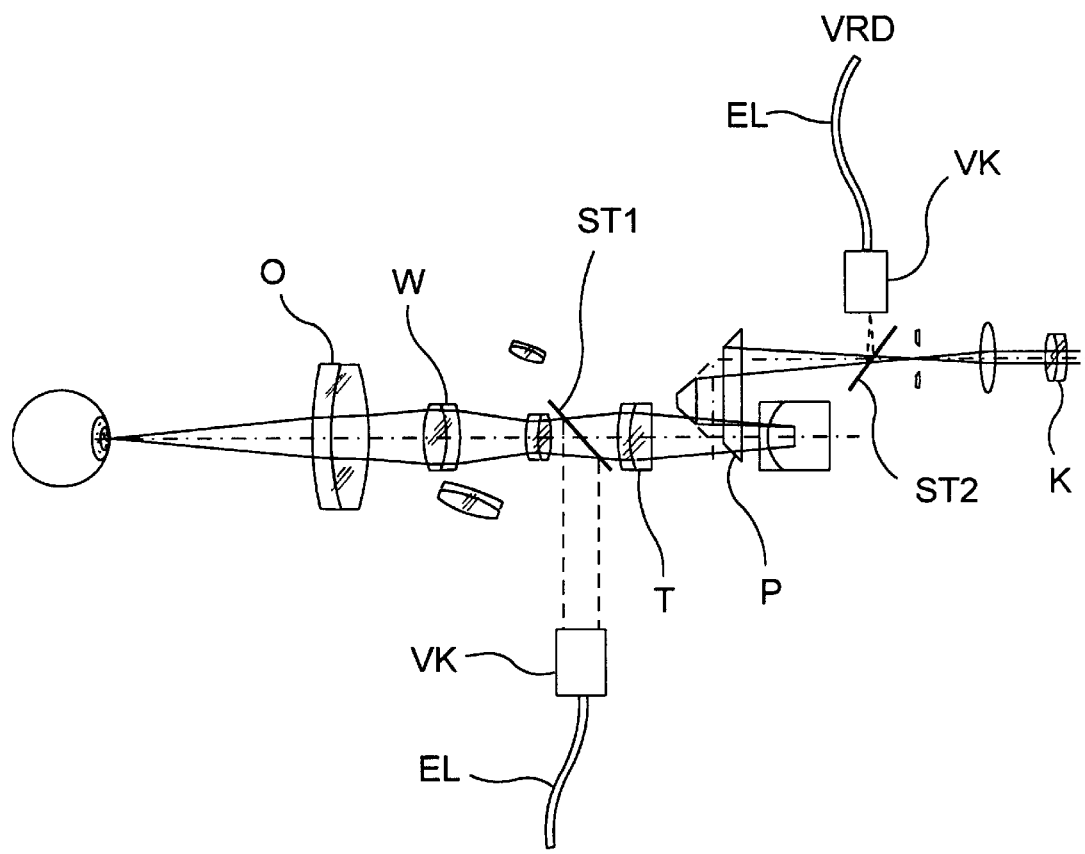
F I G. 4a
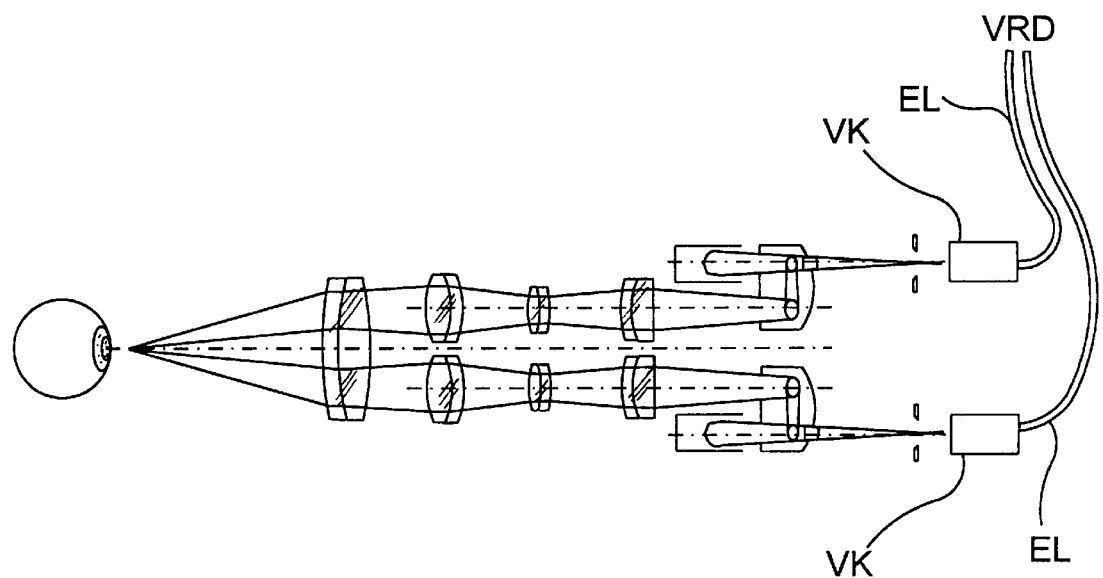
F I G. 4b

AE (TOP VIEW)

OPHTHALMOLOGICAL EXAMINATION INSTRUMENT AND METHOD FOR OPERATION THEREOF

BACKGROUND OF THE INVENTION a) Field of the Invention

The invention relate to an opthalmological examination device and a method for its use.

b) Description of the Related Art

EP 369 415 and EP 562 742 describe a "direct retinal scan display" as an alternative to optical displays such as monitors, wherein only very low outputs (not more than 20 microwatts) are required owing to direct "writing" of the image information on the fundus oculi of the observer. Video information (e.g., RGY signals) is modulated on one or more laser beams and these laser beams are deflected in the x-direction and y-direction by means of a scanner which can comprise piezocrystals, for example, and reflected in the observer's eye via a reflecting plane surface. Variable optics serve to focus the beams on the retina. The system can be used monocularly or binocularly.

U.S. Pat. No. 5,467,104 and WO 94/09472 describe a "virtual retinal display" (VRD) with high resolution and color representation. Light from a laser or a LED is modulated corresponding to video information and is projected directly onto the retina by means of a microscanner and projection optics. The reflecting element for reflecting in can be a splitter mirror, so that the projected image is superimposed on the surroundings.

A "pupil tracking system" monitors the position of the eyes and shifts the projection direction so as always to strike the pupil of the observer. A field of 140° can be presented to the observer.

In many ophthalmological applications (e.g., slit lamp, fundus camera, laser ophthalmoscope), the physician examines the various parts of the patient's eye (cornea, iris, lens, vitreous body, retina, etc.) via an optical viewer and/or a monitor. In the case of the slit lamp, a stereo microscope with a viewer is used to observe the slit image, wherein the reflection of a partial image in a video camera and display thereof on a monitor is known.

In fundus cameras, the adjustment of the fundus image is normally observed via an ocular or a monitor.

Apart from the uncomfortable body posture of the physician due to the known arrangements, it is disadvantageous that it is not possible for the physician to simultaneously see the whole patient as well as the eye, or the whole eye as well as the affected portions of the eye. A mechanically and optically complex component group is required to carry out observation. When observing the monitor, the stereo display is limited and the resolution is reduced. Stereo viewing goggles working on the shutter principle (alternating display of the image for the right and left eye) cannot provide an image free of flickering due to the system (100 Hz television technology).

Above all, when a large number of patients are seen daily, but also during a prolonged individual examination, the act of monocular viewing is very tedious for the treating physician.

OBJECT AND SUMMARY OF THE INVENTION

The primary object of the present invention is to facilitate the examination for the physician and to simultaneously improve the physician's examination possibilities. At the same time, the mechanical and optical expenditure on the corresponding examination equipment is to be reduced.

In accordance with the invention, an opthalmological arrangement comprises an opthalmological examination device for observing a patent's eye and at least one image recording unit for recording at least a part of the image of the eye generated by the examination device. An image generating unit is included which is connected with the head of an observer. Means are also included for transmitting electric signals from the image recording unit to the image generating unit. The opthalmological examination device is preferably a slit lamp or fundus camera. The image recording unit is preferably a video camera or CCD chip.

The existing video connection to a slit lamp or fundus camera is used, according to the invention, to generate the input signal for a display which is assigned to the head of the observer, preferably for a virtual retinal display as is described, for example, in the references indicated above.

The physician can accordingly observe the slit lamp images monocularly or stereoscopically, for example.

As is already known, a video camera is installed instead of the ocular viewer or a blocking out or masking is effected in the existing beam path in the direction of the video camera.

Also, the use of two video cameras enables stereoscopic viewing and accordingly enables viewing with resolution in depth.

High-resolution color viewing is enabled without the observer having to assume a compulsory posture.

The telescopic system which was normally required for magnification can be dispensed with in both monocular and stereoscopic viewing and the construction of a slit lamp is substantially simplified.

The choice of different magnifications can now be effected electronically by means of a computer arranged in an intermediate manner so that a view-finding or sighting function can be carried out at low magnification and the actual slit lamp examination can be effected at greater magnifications.

The solution according to the invention makes it possible for the physician to see both a slit lamp image and the surroundings (patient) by "reflecting into" his normal viewing field (while wearing semitransparent VRD goggles or VRD goggles which are only partially coated in a zone). Since the patient sits at a finite distance from the physician and the slit lamp image should be seen sharply at the same time as the patient, the variable optics of the VRD are used to adjust a comfortable viewing distance.

The variable optics in the VRD can accordingly not be used to compensate for defective eyesight on the part of the physician. Therefore, the physician needs to wear his corrective lenses or the deflective eyesight of the physician is compensated for by means of plug-in lenses at the VRD (analogous to a photographic camera)

An arrangement in which the lower part of the VRD serves for the projection of the slit lamp image (semitransparent or fully reflecting) while the upper part serves for spatial orientation without any optical effect is particularly advantageous.

In a fundus camera, a new kind of picture viewfinder is realized by means of the connection of a display of the kind mentioned above to the—usually—existing video connection. Monocular images can be shown and it is no longer necessary to look into an ocular or monitor. However, to present findings, a stereoscopic display of the fundus images can also be a valuable aid (e.g., depth display of the papilla. Fundus cameras with stereoscopic viewing possibilities are already known.

A division of the pupil is normally carried out in the plane of the aperture stop, e.g., by means of a set of rhomboid prisms. The two beam paths occurring as a result of the pupil division in the plane of the aperture stop form the basis for stereoscopic viewing. The connection of two video cameras after achieving pupil division which is shown in the embodiment example advantageously enables stereoscopic viewing via a VRD. The images can be recorded on video tape or digitally stored independently from the viewing by VRD.

It is also possible to carry out an on-line comparison with stored states (progressive monitoring) in a particularly advantageous manner, these stored states being superposed on the observed image. For example, it could be determined in a progressive monitoring whether pathological changes (e.g., tumors) have decreased or grown in size. For this purpose, the current picture could be presented to one eye while an earlier (stored) image could be presented to the other eye.

For laser treatment, the current image information could be supplied (from a laser slit lamp) to one eye, while the other eye receives information through the stored fundus image about the retinal area to be treated.

The construction, function and manner of operation of the invention are explained further hereinafter with reference to the schematic drawings.

DESCRIPTION OF THE PREFERRED EMBODIMENTS

According to the invention, the lens of the goggles is divided into zones Z1, Z2, wherein one zone can serve to reflect the video picture of the slit lamp SL and the second zone can serve for observing the surroundings. The observer can accordingly see the video picture of the slit lamp SL with both eyes. At the same time, however, the double reflection also enables stereoscopic viewing, which will be discussed hereinafter.

Figure 3:
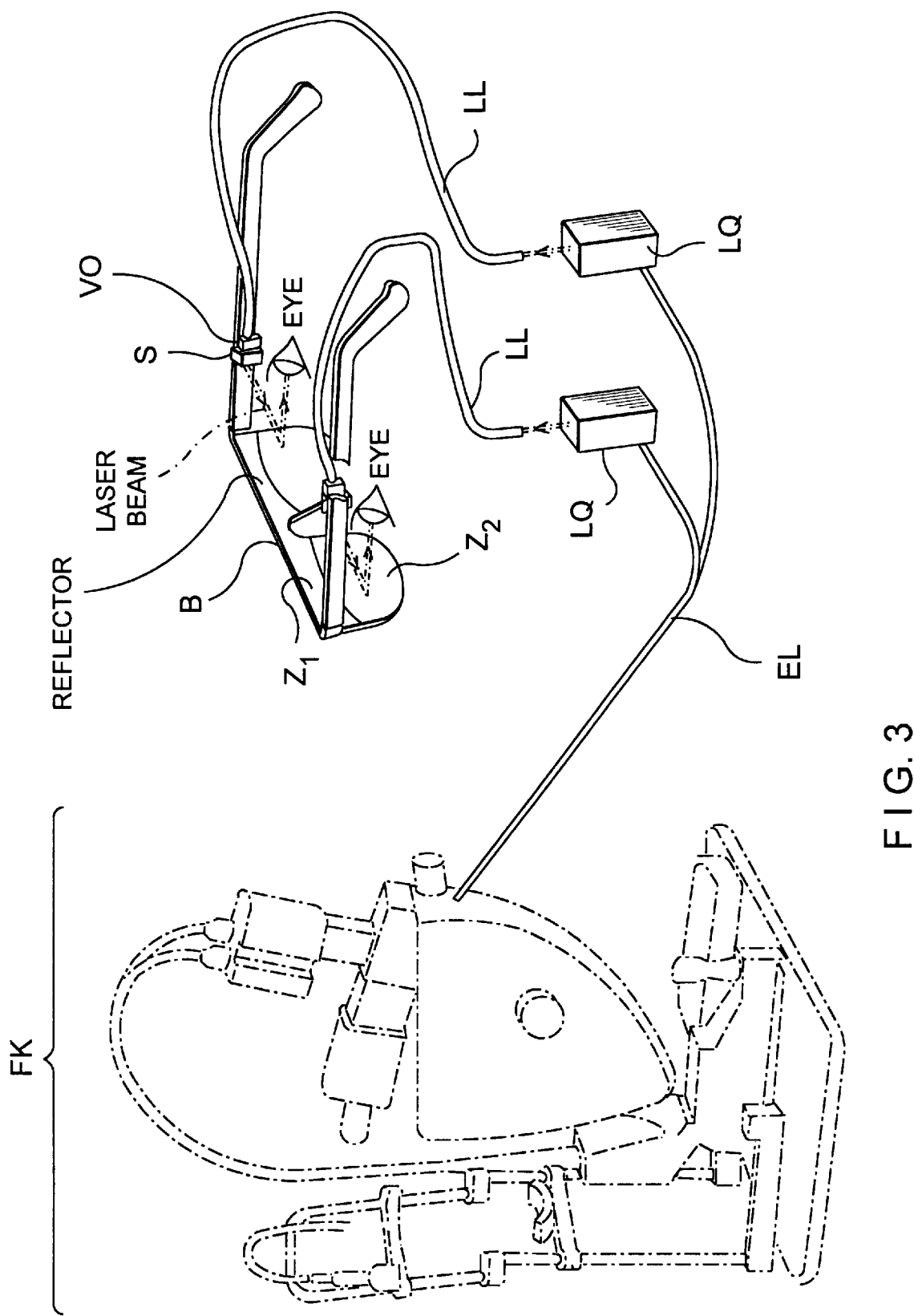

FIG. 3 shows the coupling out of a video signal in the direction of the viewing goggles B via signal lines EL from a fundus camera FK with video attachment.

With reference to the ZEISS publication "Eye Examinations with the Slit Lamp", No. 313116-7560.146 of 1996, FIG. 4a shows a slit lamp microscope which works on the principle of a telescopic lens. There is a separate parallel beam path between an objective O and tube lens T for each eye of the observer. A telescopic system W is arranged between the objective O and tube lens T for each beam path for varying the total magnification. The intermediate images projected by the tube lenses T via the following rotatable prisms P are observed with the oculars K.

Figure 1:
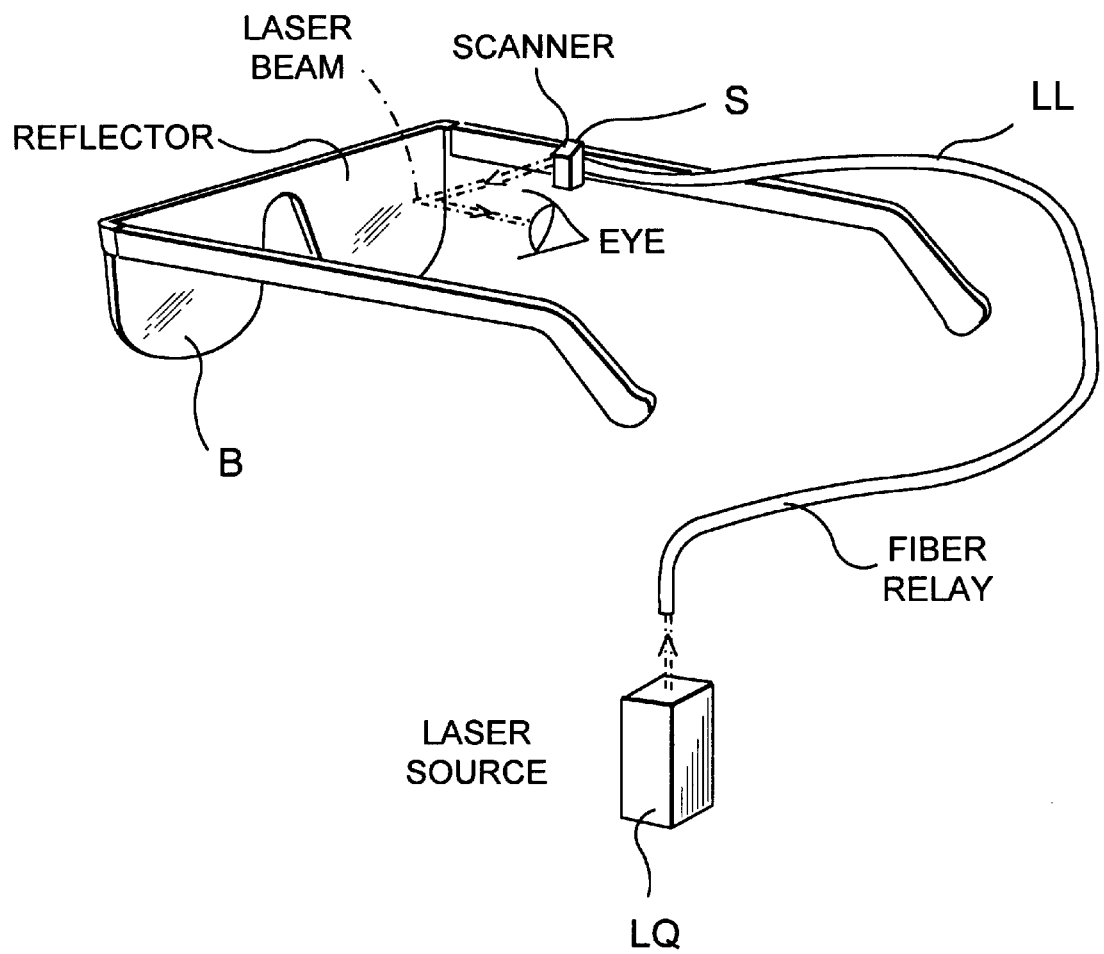
FIG. 1 shows a construction of goggles B to which is fastened a scanner S, the light of a laser light source LQ being transmitted to the scanner S by means of a flexible light guide LL. The lenses of the goggles are partially coated and the image generated by the scanner S is reflected directly into the retina
Figure 2:
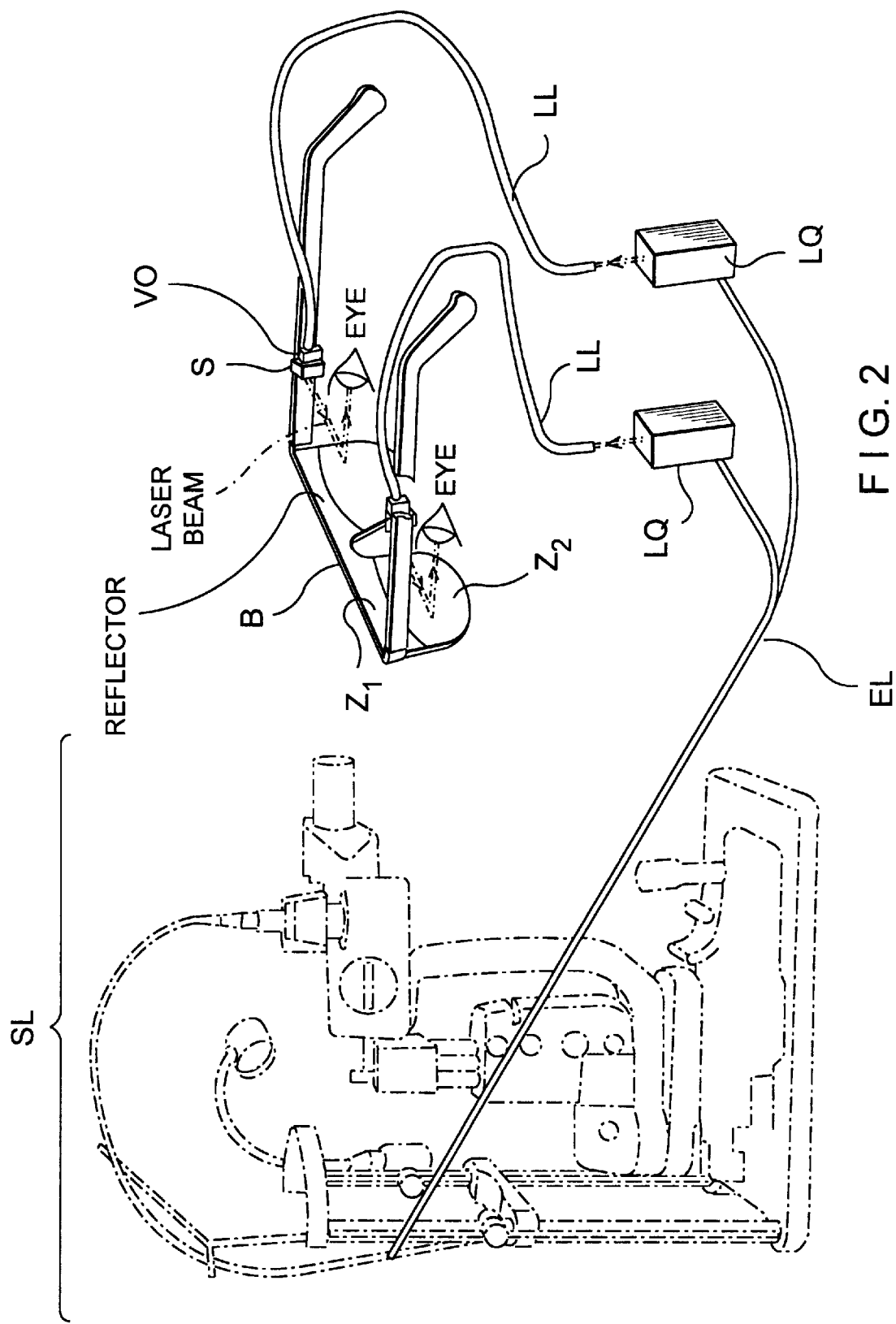
FIG. 2 shows a known slit lamp construction SL with a video camera VK connected to the viewing optics, wherein the video signal is transmitted to the goggles B via lines EL. The goggles B have scanners S for both of the viewer's eyes with variable optics VO being associated with these scanners S.

In this case, the observation beam path can be coupled out in the direction of the video camera VK, e.g., at locations ST1 or ST2, this video camera VK being connected, via lines EL, with a retinal display according to the illustrations in FIGS. 1 to 3.

According to FIG. 4b showing a top view of 4a, stereoscopic viewing is made possible in that video cameras VK are provided for the respective intermediate images instead of the oculars K and the two video signals according to FIG. 3 are reflected in the associated eyes of the observer to generate a stereo picture. A magnification change can be advantageously produced in the electronically transmitted picture so that the telescopic system W could be dispensed with.

Figure 4C:
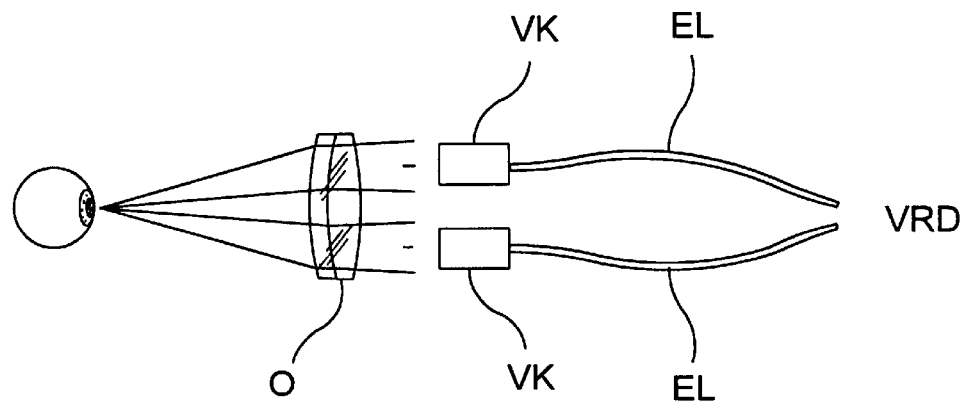

FIG. 4c shows a further simplified arrangement which comprises video cameras directly following the objective O and having imaging optics whose signal is transmitted to the observer goggles.

Figure 5B:
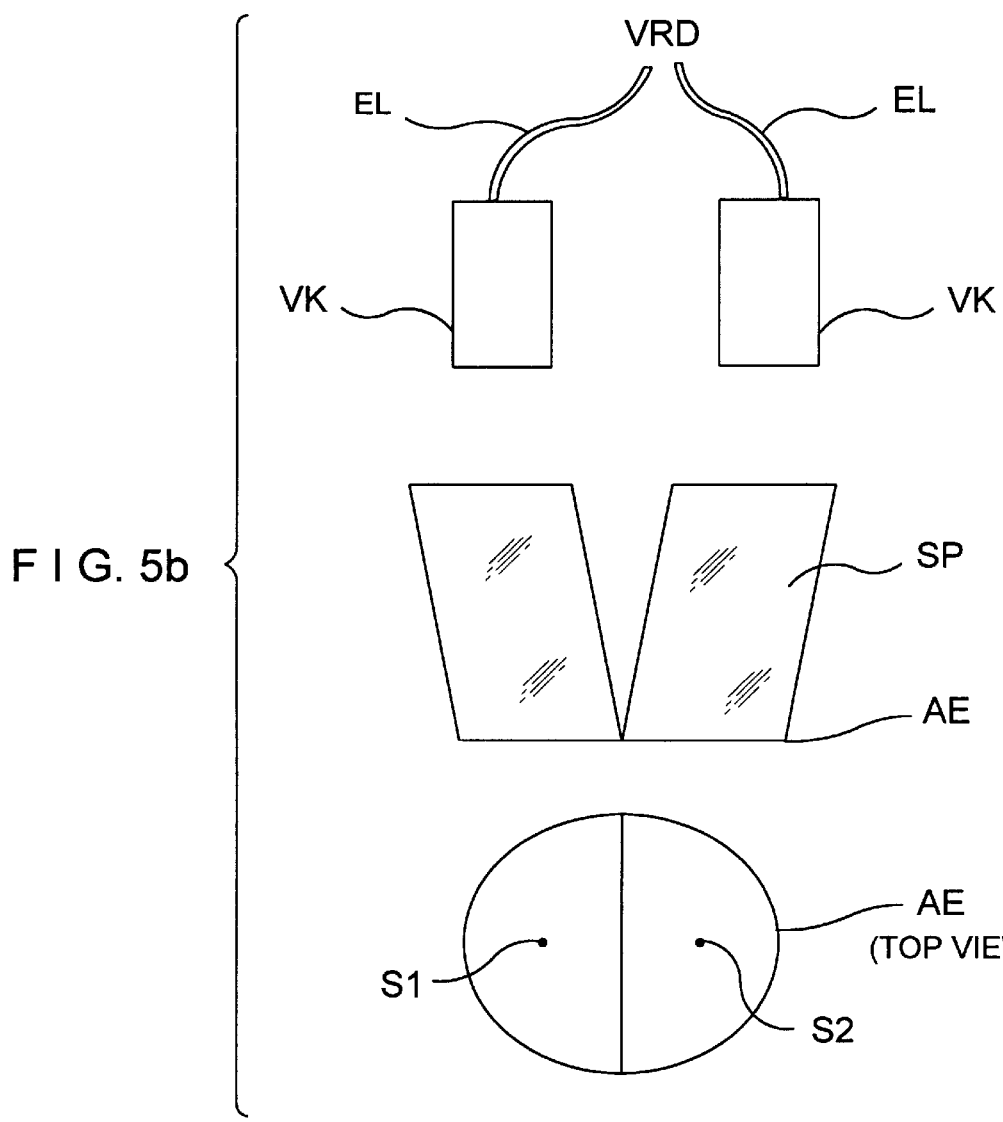
Figure 5A:
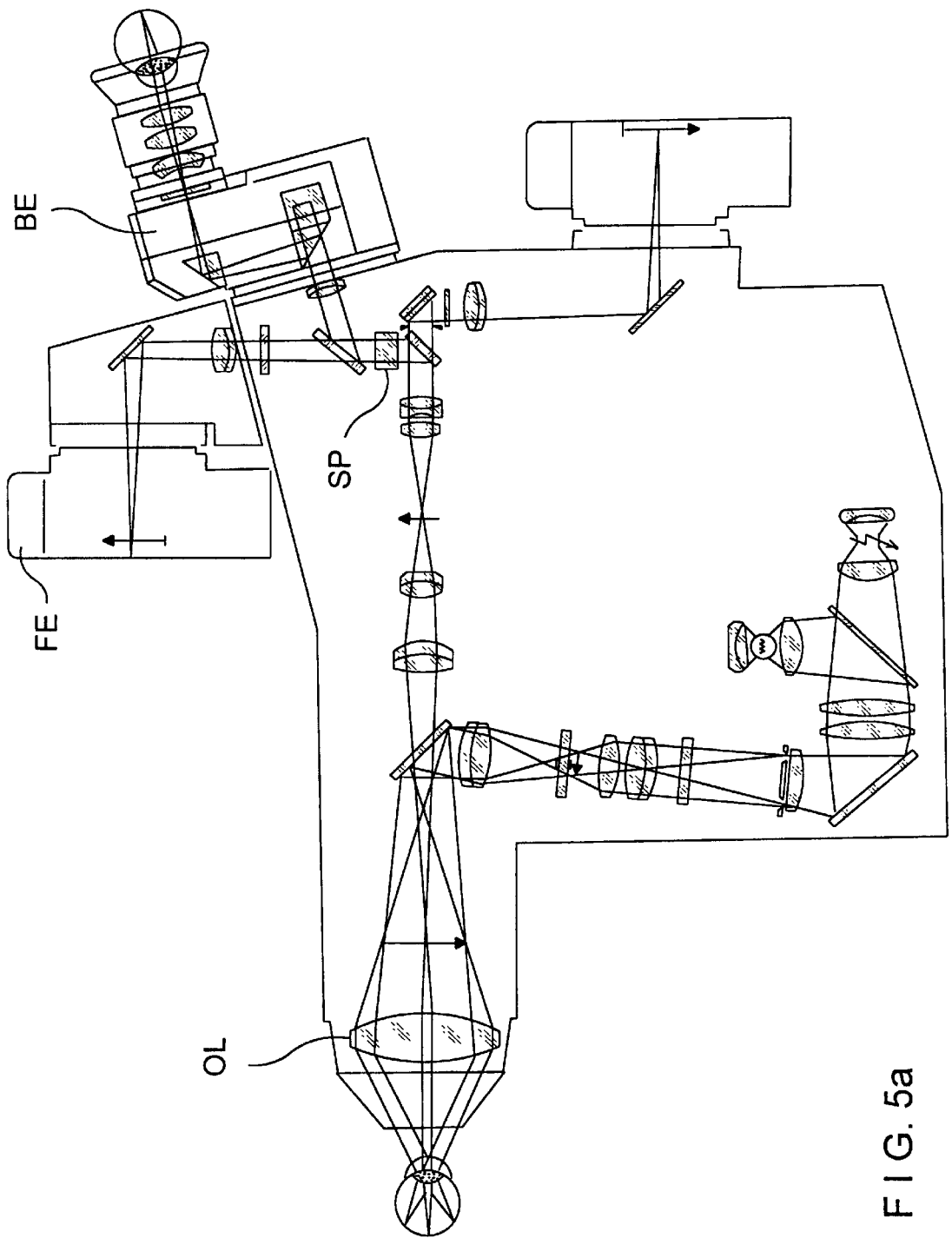

With reference to the article "New Retina Camera from Jena", published in the periodical Augenoptik, Berlin 104 (1987), FIG. 5a shows the optical diagram of a stereoscopic fundus camera, wherein a binocular viewer BE is provided to which stereoscopic partial beam paths of an ophthalmoscope lens OL are transmitted via a stereo prism SP. A photographic device FE makes it possible to record stereo pictures.

FIG. 5b shows a schematic side view of the stereo prism SP as a rhomboid prism, where AE represents the plane of the aperture stop and S1, S2 represent the centers of gravity of the stereoscopic partial beams.

Figure 5C:
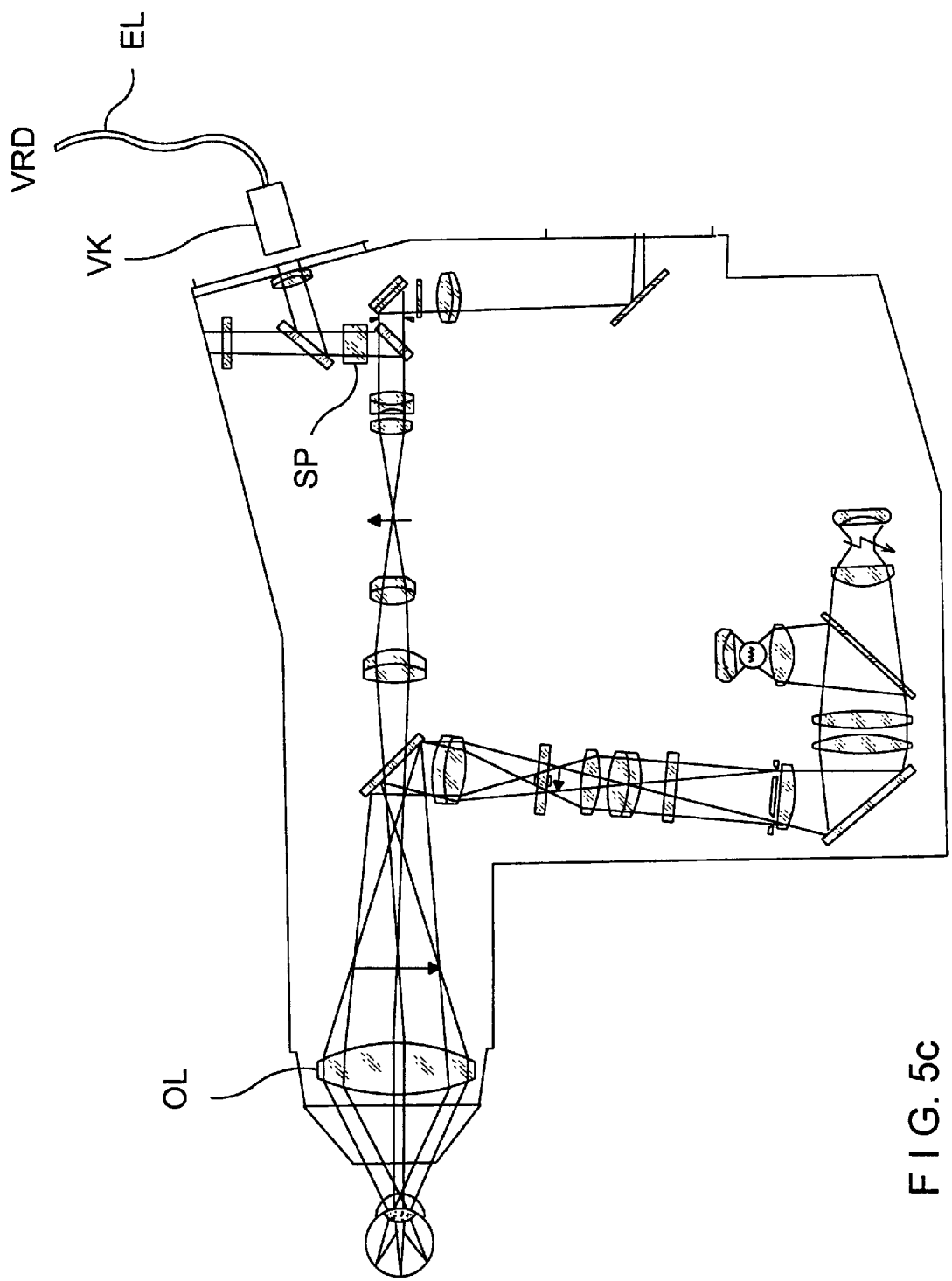

As is shown in FIGS. 5b and 5c, video cameras VK or CCD-chips (5c) whose signal is transmitted to the observer goggles B for generating the stereoscopic image can be arranged, according to the invention, on the stereoscopic fundus camera after the stereo prism SP. The binocular viewer BE is accordingly dispensed with. The photographic device FE can also be dispensed with in an advantageous manner due to the possibility of the digital image storage of the generated video signals (S1 and S2 in FIG. 5b/left and right channels are stored separately).

While the foregoing description and drawings represent the present invention, it will be obvious to those skilled in the art that various changes may be made therein without departing from the true spirit and scope of the present invention.

What is claimed is:

1. An opthalmological arrangement comprising:

an opthalmological examination device for observing a patient's eye;

at least one image recording unit for recording at least a part of the image of the eye generated by the examination device;

an image generating unit connected with the head of an observer; and means for transmitting electric signals from the image recording unit to said image generating unit.

2. The arrangement of claim 1, wherein said opthalmological examination device is a slit lamp.

3. The arrangement of claim 1, wherein said opthalmological examination device is a fundus camera.

4. The arrangement of claim 1, wherein said image recording unit is a video camera.

5. The arrangement of claim 1, wherein said image recording unit is a CCD chip.

6. The arrangement of claim 1, wherein said image generating unit includes means for raster-shaped projections by at least one laser.

7. The arrangement of claim 1, wherein said image generating unit includes means for generating two pictures which are associated with the two eyes of the observer.

8. The arrangement according to claim 1, including capability for stereoscopic observation by two image recording units.

9. The arrangement of claim 8, including two video cameras.

10. The arrangement according to claim 8, including two CCD chips.

11. The arrangement according to claim 1, wherein the image generating unit is a component part of observer goggles.

12. The arrangement according to claim 11, wherein at least one light guide is fastened to the observer goggles, which light guide projects an image on an eye of an observer which is generated by at least one laser arrangement and at least one scanner.

13. The arrangement according to claim 11, wherein the lenses of the observer goggles are at least partially coated.

14. The arrangement according to claim 11, wherein the lenses of the observer goggles are divided into zones and at least one zone is at least partially coated.

15. The arrangement according to claim 1, wherein at least one image generating scanner is arranged at the observer goggles.

16. The arrangement according to claim 1, including variable optics associated with said scanner.

17. The arrangement according to claim 1, wherein refraction is compensated for the observer by additional spectacles.

18. The arrangement according to claim 1, wherein refraction is compensated for the observer by exchangeable lenses.

19. A method for operating an image generating unit of the type used in an opthalmological arrangement comprising:

an opthalmological examination device for observing a patient's eye;

at least one image recording unit for recording at least a part of the image of the eye generated by the examination device;

an image generating unit connected with the head of an observer; and means for transmitting electric signals from the image recording unit to said image generating unit, said method comprises the steps of:

superimposing additional information generated by a computer via the image generating unit on a first image generated from electrical signals of said image recording unit at least for one eye of the observer; and/or superimposing a second image which is modified with respect to color, contrast or other image features for presentation to the observer, as an additional image on the other respective eye or the first image for one or both eyes of the observer.

20. The method of claim 19, wherein the additional information comprises stored images.

21. The method of claim 19, wherein the additional information comprises stored previous recordings.

22. The method of claim 19, wherein the additional information comprises physiological data on the patient.

\* \* \* \* \*

UNITED STATES PATENT AND TRADEMARK OFFICE
CERTIFICATE OF CORRECTION

PATENT NO. : 5,914,770

DATED : June 22, 1999

INVENTOR(S) : Roland Bergner, et al.

It is certified that error appears in the above-identified patent and that said Letters Patent is hereby corrected as shown below:

Column 3, below line 41, insert:

-- FIG. 3 is a part pictorial and part schematic representation showing the coupling out of the video signal in the direction of the viewing goggles;

FIG. 4a is a schematic representation of a slit lamp microscope with an indication of where the observation beam path may be coupled out of in the direction video camera;

FIG. 4b is a schematic top view of FIG. 4a;

FIG. 4c shows a further simplified arrangement in schematic form where video cameras directly follow the objective whose signal is transmitted to the observer goggles;

FIG. 5a is a schematic representation of a stereoscopic fundus camera which may be used in the present invention;

FIG. 5b is a simplified schematic top view of FIG. 5a showing the development of signals for use with observer goggles in accordance with the invention; and

UNITED STATES PATENT AND TRADEMARK OFFICE
CERTIFICATE OF CORRECTION

PATENT NO. : 5,914,770

DATED : June 22, 1999

INVENTOR(S) : Roland Bergner, et al.

It is certified that error appears in the above-identified patent and that said Letters Patent is hereby corrected as shown below:

FIG. 5c indicates in schematic form how the binocular viewer may be dispensed with in the camera of FIG. 5a in accordance with the present invention.--

Signed and Sealed this

Fifth Day of October, 1999

Attest:

Attesting Officer

Q. TODD DICKINSON

Acting Commissioner of Patents and Trademarks